United States Patent
Heinrich et al.

(10) Patent No.: US 10,224,119 B1
(45) Date of Patent: Mar. 5, 2019

(54) SYSTEM AND METHOD OF PREDICTION THROUGH THE USE OF LATENT SEMANTIC INDEXING

(71) Applicant: Quire, Inc. (Delaware corporation), Memphis, TN (US)

(72) Inventors: Kevin Erich Heinrich, Collerville, TN (US); Ramin Homayouni, Memphis, TN (US); Bradford Ryan Silver, Memphis, TN (US)

(*) Notice: Subject to any disclaimer, the term of this patent is extended or adjusted under 35 U.S.C. 154(b) by 1103 days.

(21) Appl. No.: 14/494,582

(22) Filed: Sep. 23, 2014

Related U.S. Application Data (60) Provisional application No. 61/908,364, filed on Nov. 25, 2013.

(51) Int. Cl.
   *G06F 17/30* (2006.01)
   *G16H 50/70* (2018.01)

(52) U.S. Cl.
   CPC ........ *G16H 50/70* (2018.01); *G06F 17/30663* (2013.01); *G06F 17/30684* (2013.01)

(58) Field of Classification Search
   CPC .. G06F 17/2785; G06F 17/2795; G06F 17/28; G06F 17/30011; G06F 17/30336; G06F 17/30616; G06F 17/277; G06F 17/30864; G06F 17/30401; G06F 17/30684
   See application file for complete search history.

(56) References Cited

U.S. PATENT DOCUMENTS

| | | |
|---|---|---|
| 4,839,853 A | 6/1989 | Deerwester et al. |
| 7,813,937 B1 | 10/2010 | Pathria et al. |

OTHER PUBLICATIONS

Roque, Francisco S., et al., Using Electronic Patient Records to Discover Disease Correlations and Stratify Patient Cohorts, PLoS Computational Biology (Aug. 2011), 10 pages, vol. 7, Issue 8, Public Library of Science (San Francisco, California, U.S.A.).

Kansagara, Devan, et al., Risk Prediction Models for Hospital Readmission—A Systematic Review, JAMA (Oct. 19, 2011), pp. 1688-1698, vol. 306, No. 15, American Medical Association (Chicago, Illinois, U.S.A.).

Ohno-Machado, Lucila, Realizing the Full Potential of Electronic Health Records: The Role of Natural Language Processing, J. Am. Med. Inform. Assoc. (Sep. 2011), p. 539, vol. 18, No. 5, BMJ Publishing, Inc. (London, United Kingdom).

*Primary Examiner* — Maroun P Kanaan
(74) *Attorney, Agent, or Firm* — John L. Sotomayor

(57) ABSTRACT

A predictive modeling method implemented on a computer for predicting patient outcomes and conditions from medical database records of a population of patients, and an optimization process of iterative variation of parameters of the method to achieve a best precision fit. Individual patient documents are created by concatenation of unstructured text fields from the patient's medical record, and these are processed using Natural Language Processing. A patient document corpus is built, and terms in the corpus are weighted and mapped to standard vocabularies. A term-by-document matrix is built and its dimensionality is reduced by Latent Semantic Indexing. Patient and term queries are combined and scored, producing a ranked list. The parameters of the model are iteratively optimized for an input list of patients with corresponding health score values.

3 Claims, 7 Drawing Sheets

SYSTEM AND METHOD OF PREDICTION THROUGH THE USE OF LATENT SEMANTIC INDEXING

CROSS REFERENCE TO RELATED APPLICATIONS

This application is a continuation-in-part, and claims priority benefit, of U.S. Provisional Patent Application No. 61/908,364 (filed Nov. 25, 2013), entitled "System and Method of Prediction through the Use of Latent Sematic Indexing" (sic), fully incorporated by reference herein.

STATEMENT REGARDING FEDERALLY SPONSORED RESEARCH OR DEVELOPMENT

Not applicable.

REFERENCE TO COMPACT DISC(S)

Not applicable.

BACKGROUND OF THE INVENTION

1. Field of the Invention

The present invention relates to a system and method that analyzes medical database records of a population of patients, summarizes those medical records, and provides predictions based on the medical records.

2. Information Disclosure Statement

In order to improve health care delivery, there is a growing need to understand patient characteristics beyond what is contained in the structured fields in medical records. Structured fields include lab test values, diagnosis codes, billing codes, etc. There is also a growing need to analyze the full amount of information in medical records in order to more accurately predict outcomes and reveal opportunities for early interventions in a particular patient and/or specific group of patients. Most medical records contain a vast amount of unstructured text (such as physician notes, discharge summaries, etc.) which are not easily accessible for automated data analysis. The value of the unstructured text in medical records is beginning to be explored in the scientific research domain. To date, most of this effort is focused on using Natural Language Processing ("NLP") techniques to retrieve information from the unstructured text and to map them into structured fields. NLP is being used in clinical decision support to identify adverse events associated with drugs and vaccines or detection of sepsis in a clinical setting. Ohno-Machado, "Realizing the full potential of electronic health records: the role of natural language processing", J. Am. Med. Inform. Assoc. Vol 18, No 5 (September 2011). In addition, NLP has been effectively used to combine information in unstructured text with International Classification of Disease (ICD10) ontology to stratify and classify patient cohorts. Roque et al., "Using electronic patient records to discover disease correlations and stratify patient cohorts", PLoS Computational Biology 7(8): e100214 (August 2011).

Predictive modeling has been utilized in healthcare for several decades. Statistical approaches such as linear regression, mixed-effects, and Bayesian models can be trained on a set of patients with a given outcome using discrete data from their medical records (such as lab values, vital signs, ICD10 and CPT codes, etc.) and then applied to a new set of patients to predict specific outcomes. A large variety of statistical models have been reported that predict adverse events, infections, hospital admissions, cost, or risk of chronic diseases and complications. For example, in a systematic review by Kansagara et al., 26 unique models were identified that predict readmission risk using clinical and/or administrative data. Kansagara et al., "Risk Prediction Models for Hospital Readmission—A Systematic Review" JAMA 306(15):1688-1698 (Oct. 19, 2011). Current modeling approaches use structured fields in medical records that are highly specific to a given condition and are not generalizable to other conditions. Such a prior art approach requires considerable effort by medical and statistical experts to produce a condition-specific predictive model.

Deerwester et al., U.S. Pat. No. 4,839,853 (issued Jun. 13, 1989), discloses an information retrieval method called Latent Semantic Indexing ("LSI") that is used in the present invention.

Pathria et al., U.S. Pat. No. 7,813,937 (issued Oct. 12, 2010), discloses the use of LSI as applied to medical claims data for detection of consistency and fraud.

It is therefore desirable to have a fully-automated method that can analyze unstructured text in medical records and that is flexible enough to be applied to substantially any condition or outcome without the need of human experts to design and fine-tune the analytical model.

None of these prior art references, either singly or in combination, discloses or suggests the present invention.

BRIEF SUMMARY OF THE INVENTION

The present invention is an automated method that utilizes the vast amount of descriptive and unstructured text in medical database records in order to characterize patient populations and to accurately predict any set of conditions or outcomes. The system involves a plurality of aspects or major steps.

In a first major step of the method of the present invention, individual patient documents are created by concatenation of all unstructured text fields from the patient's medical records. The concatenated patient record is then processed using standard Natural Language Processing ("NLP") approaches to remove redundancies, negations, etc. Next, a collection (corpus) is built that contains documents for the entire population of patients, or a subset of patients, within a health system.

In a second major step of the method of the present invention, terms in documents are given weights such that they provide a specific summary of each patient. These terms can be mapped to standard vocabularies (ICD9, SNOMED, FDA drug lists, etc.) to quickly characterize the patient.

In a third major step of the method of the present invention, Latent Semantic Indexing ("LSI") is performed on the document collection to reduce the dimensionality of the document-by-term matrix. The reduced matrix produces a "concept" space in which patients or terms can be represented. A computer system implementing the method of the present invention has been developed to provide a graphical interface for users to interact with the LSI model in real time. Using the method of the present invention, patients can be ranked based on conceptual relatedness to any individual or plurality of keywords. In addition, patients can be ranked based on conceptual relatedness to any individual or plurality of individual patients.

A fourth major step of the method of the present invention involves combining and scoring a set of terms and/or patient queries at a range of relatedness values to produce a final list of ranked patients who have high relationship to the query set.

A fifth major step of the method of the present invention involves training and optimizing a predictive model that utilizes concepts extracted from medical records pertaining to a set of patients with known outcomes and then applying them to a new set of patients to predict future outcomes.

It is an object of the present invention to provide a fully-automated method that can analyze unstructured text in medical records of a population of patients and predict future outcomes, and that is flexible enough to be applied to substantially any condition or outcome without the need of human experts to design and fine-tune the analytical model.

DETAILED DESCRIPTION OF THE INVENTION

Figure 1:
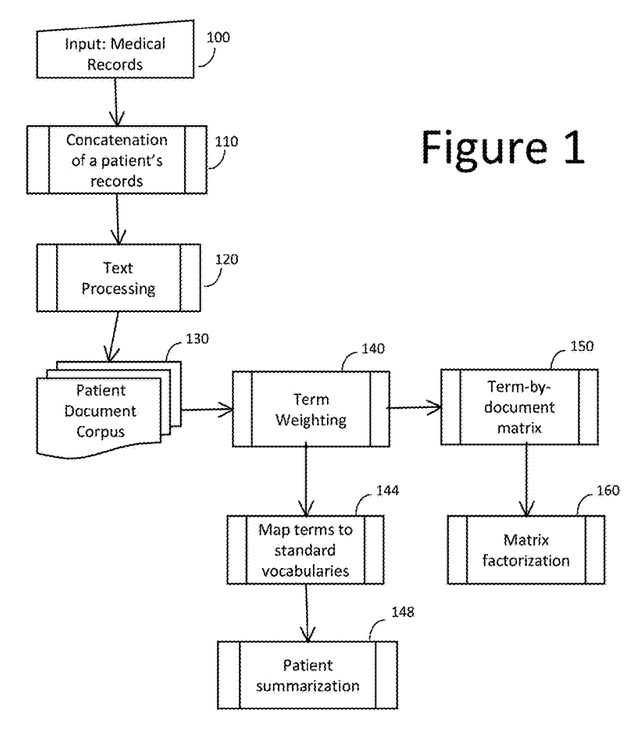
FIG. 1 is a flowchart representing the process of building a patient document corpus which is used to calculate term weights, summarize patients and perform matrix factorization to represent patients and keywords in reduced dimensions (concept space).

Referring to FIG. 1, the method of the present invention is implemented on a well-known computer system, and receives an input of medical records 100, typically in XML format, from a healthcare system for a multiplicity of patients. The unstructured text fields for individual patients are extracted from records dating back to the earliest encounter of that patient in the health system. The text from all patient encounters is then concatenated into a concatenated document 110. The document is then processed using NLP methods in step 120 to remove lab results, negations (e.g., patient does not have diabetes, or the test result is negative for HIV, etc). In addition, only a single history and physical result is represented for each patient in a patient document. The result of this text processing of all patient documents for the multiplicity of patients in the healthcare system is a collection of documents represented as a patient document corpus 130. Standard term weighting (e.g., tf-idf, log entropy, etc.) is applied to this corpus in step 140, such that each term in the corpus is assigned a weight representing the frequency of the term in the patient's document with respect to the frequency of the term across all documents in the corpus. In step 144, weighted terms are mapped to a variety of standard vocabularies or ontologies (e.g. ICD9, CPT, SNOMED, FDA drug list, etc). Highly-ranked terms and vocabulary/ontology classifications are then produced by the invention as a patient summarization 148 in order to quickly summarize the highly relevant characteristics of the patient. Also, using the weighted terms, a high-dimensional and sparse term-by-document matrix 150 is constructed in which each term in the corpus is represented as a vector across the entire population of patients. Similarly, a patient can be represented as a vector of weighted terms in the term-by-document matrix 150. Finally, matrix factorization methods such as LSI (singular value decomposition or principle component analysis) or non-negative matrix factorization is performed to reduce the dimensionality of the matrix into a lower-dimensional matrix "concept space" 160. In this manner, a patient can be represented as a highly specific 'bag of words' that can be used to derive relationships.

Figure 2:
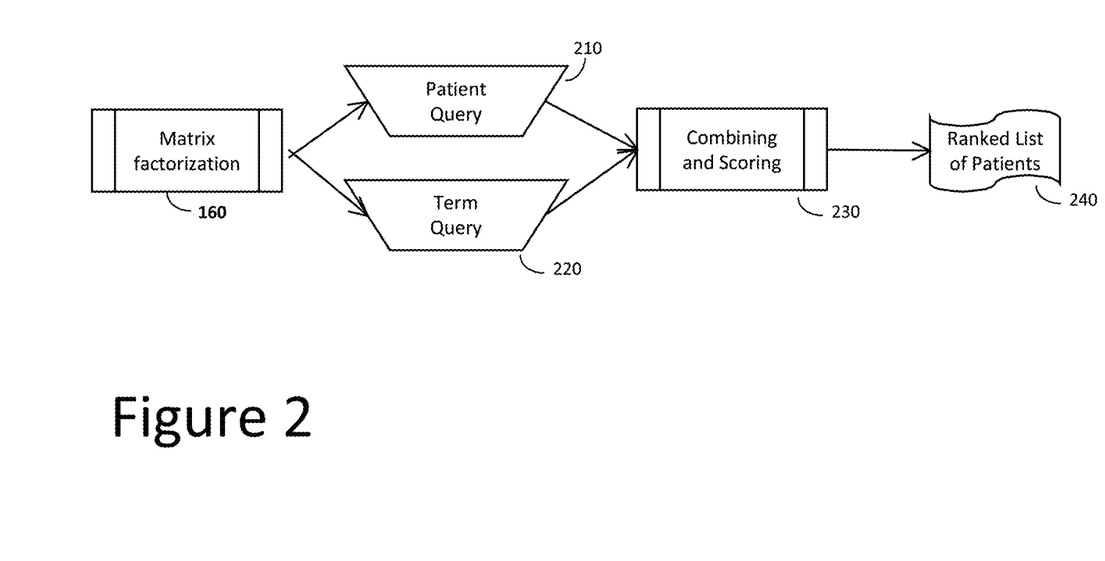
FIG. 2 is a flowchart representing the process of querying the patient concept matrix, combining and scoring multiple queries, and producing a ranked (prioritized) list of patients based on relevancy to the queries.

Referring to FIG. 2, this lower dimensional matrix 160 intermediate result can be queried using any term or combination of terms 220 to rank patients in the corpus according to literal or conceptual relatedness to the query using a similarity score. Likewise, an entire patient document 210 can be used to rank other patients in the corpus according to relatedness to the query using a similarity score. Each type of query produces a single ranking of all patients in the corpus along with a similarity score. In step 230, given a single threshold of the similarity score, multiple queries can be combined in tabular format and used to re-rank the population of patients in the corpus based on relatedness to multiple queries. In this manner, a final ranked list 240 is provided in which high ranking patients have similarity to a subset of the queries provided by the user.

Figure 3:
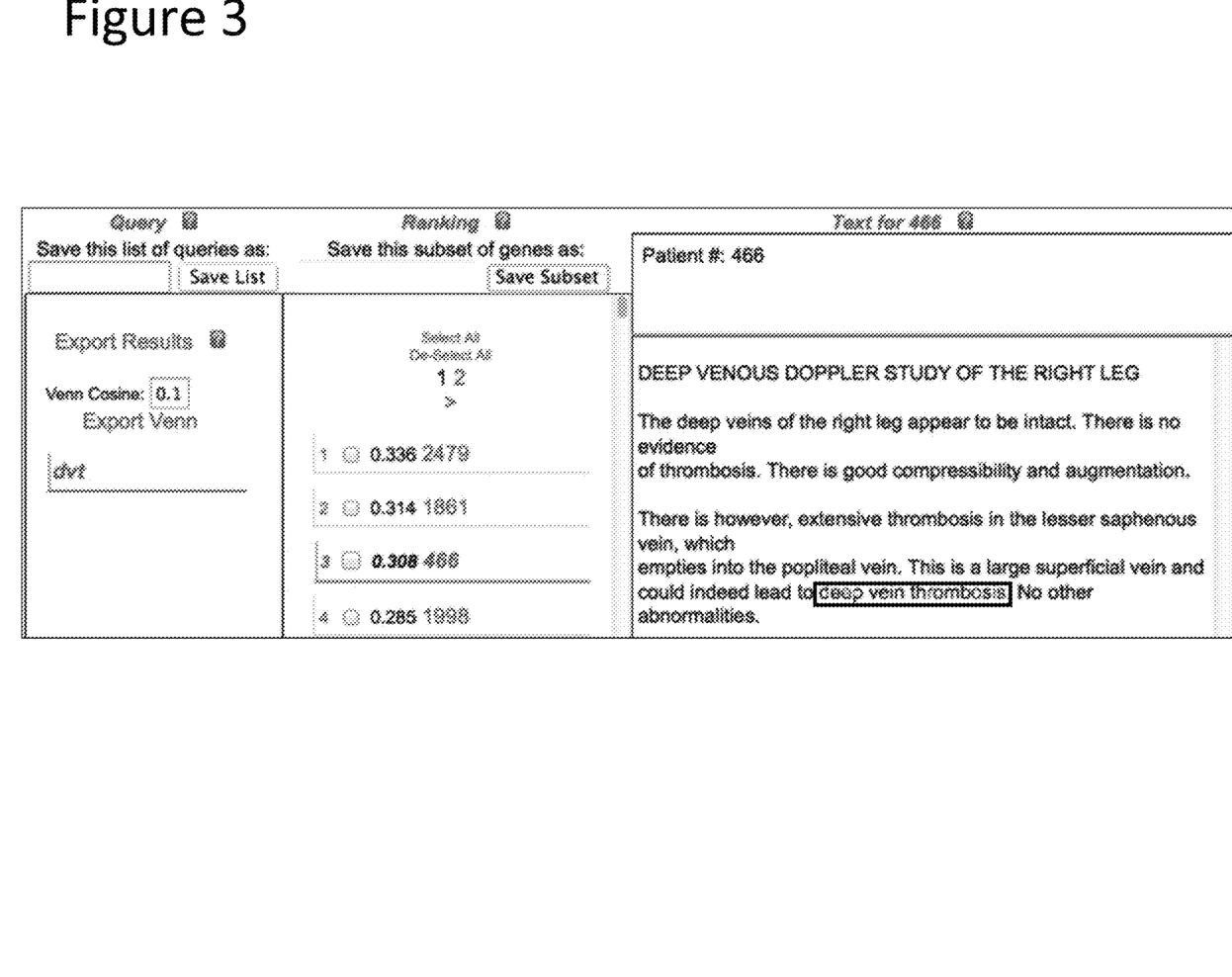
FIG. 3 is an embodiment of the system and method of the present invention that ranks patients based on conceptual similarity to a single or plurality of queries, where a query can be any term, combination of terms, entire patient record, or combination of patient records.

FIG. 3 provides an example screenshot showing where the query 'dvt' (abbreviation for deep vein thrombosis) was used to rank all patients in the corpus. Patients that are highly-ranked by the system typically contain the actual query 'dvt' in the medical record. However, it is important to note that the system also highly ranks patients even if the term 'dvt' is not explicitly mentioned in the medical record, such as patient #466 in the example shown in FIG. 3. Therefore, the system is able to deduce synonyms automatically based on conceptualization of the unstructured text as a result of LSI.

Figure 4:
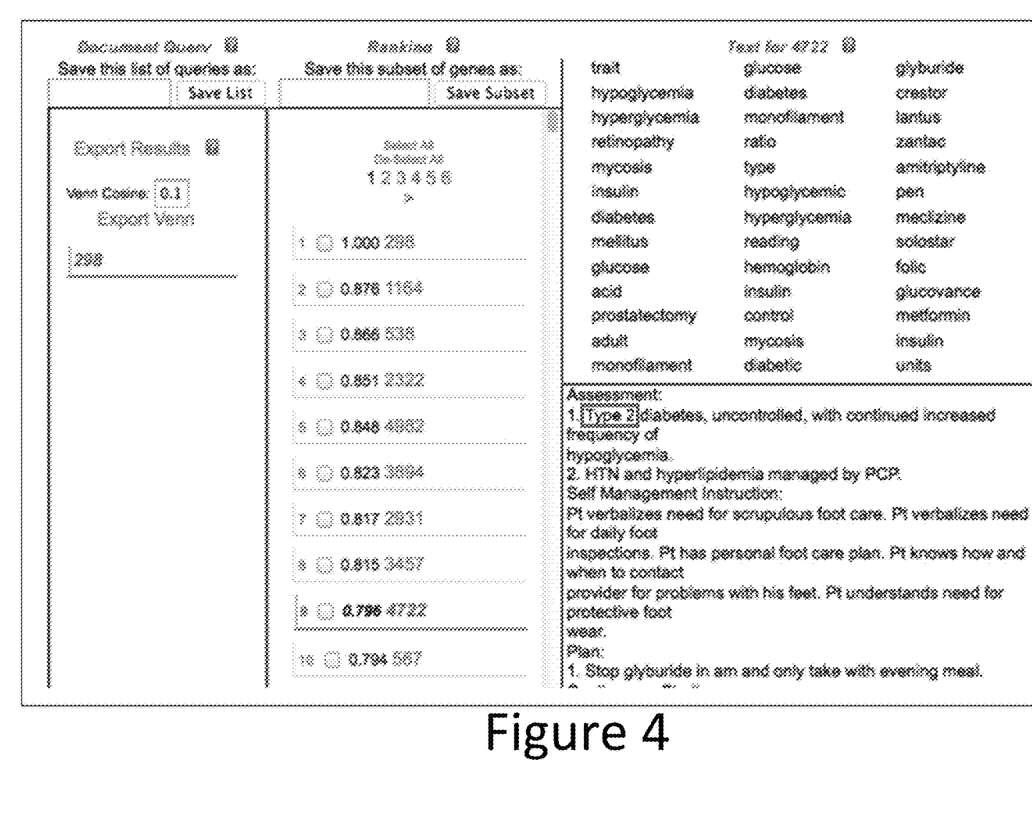
FIG. 4 is an embodiment of the system and method of the present invention that produces a ranked list of patients in a given population according to semantic similarities to multiple queries.

FIG. 4 provides an example screenshot showing where the query is an entire patient document (patient #298). In this case, all patients in the population are ranked based on a similarity score which is derived from a combination of all weighted words in the query patient's record. For instance, the primary diagnosis of patient #298 is Type-2 Diabetes. The system returns patients who also have Type-2 diabetes, such as patient #4722 (ranked 9 on the list). Also, note that the system summarizes the patients automatically by listing top ontology terms mapped to weighted terms extracted from the patient's medical record. In this example, SNOMED filtered terms such as hypoglycemia, hyperglycemia, retinopathy etc., are displayed on the left column of the upper right hand panel in FIG. 4. In addition, the top-ranked drugs such as Crestor, Lantus, Zantac, etc., associated with this patient are listed in the right column, shown in the upper right hand panel of FIG. 4.

Figure 5:
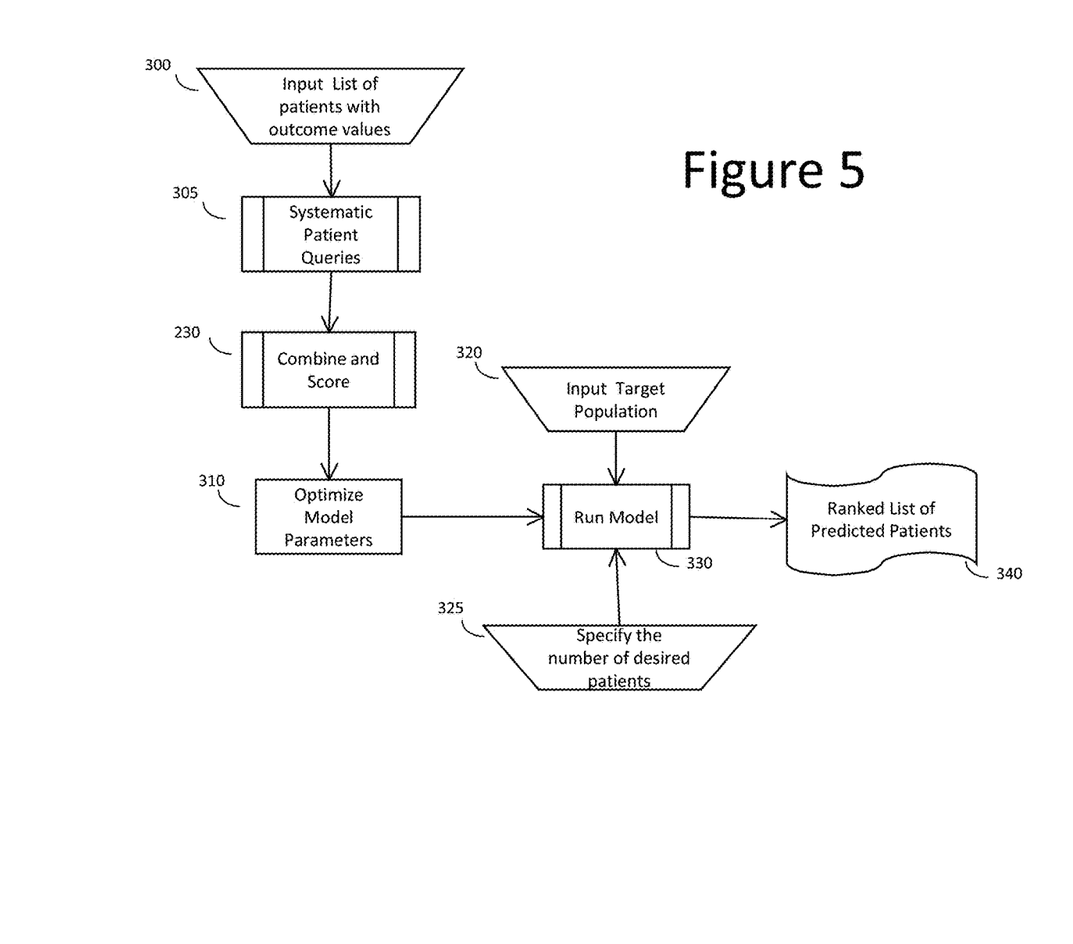
FIG. 5 is a flowchart representing the process of predictive modeling, where the model is trained based on a set of patients from the population corpus with the desired characteristics or outcomes. The model is optimized and applied to a new population of patients to produce a ranked list of patients with high likelihood of having the desired condition or outcome.

FIG. 5 shows the workflow for the predictive modeling system. The system requires that users provide a list of patients with corresponding outcome values 300. Outcome values may be admission frequencies, Risk Adjusted Factor scores, Hierarchical Condition Category scores, or any other type of health score. In step 305, systematic patient queries are performed against the entire population of patients, starting from the highest-ranked patient and combinations thereof, based on the outcome values provided by the user. The results of the queries are combined in step 230 as described hereinbefore in connection with FIG. 2. The optimized model 310 considers the following five independent parameters:

1) the number of patients used for the query,
2) the threshold for the similarity score,
3) the frequency of association to query patients,
4) the recall value of the patients returned, and
5) the precision value of the patients returned.

Optimization step 310 finds the optimal parameters for predicting the desired outcome on the current or training population. Using these five independent parameters, the method of the present invention iterates through a variation of the parameters to achieve a best precision fit. The optimized predictive model 330 can then be run on a new set of patients 320 or the existing set of patients, considering the desired number of patients by the user 325. Finally, the method of the present invention provides a ranked list of patients 340 that have the highest likelihood of the desired outcome.

Figure 6:
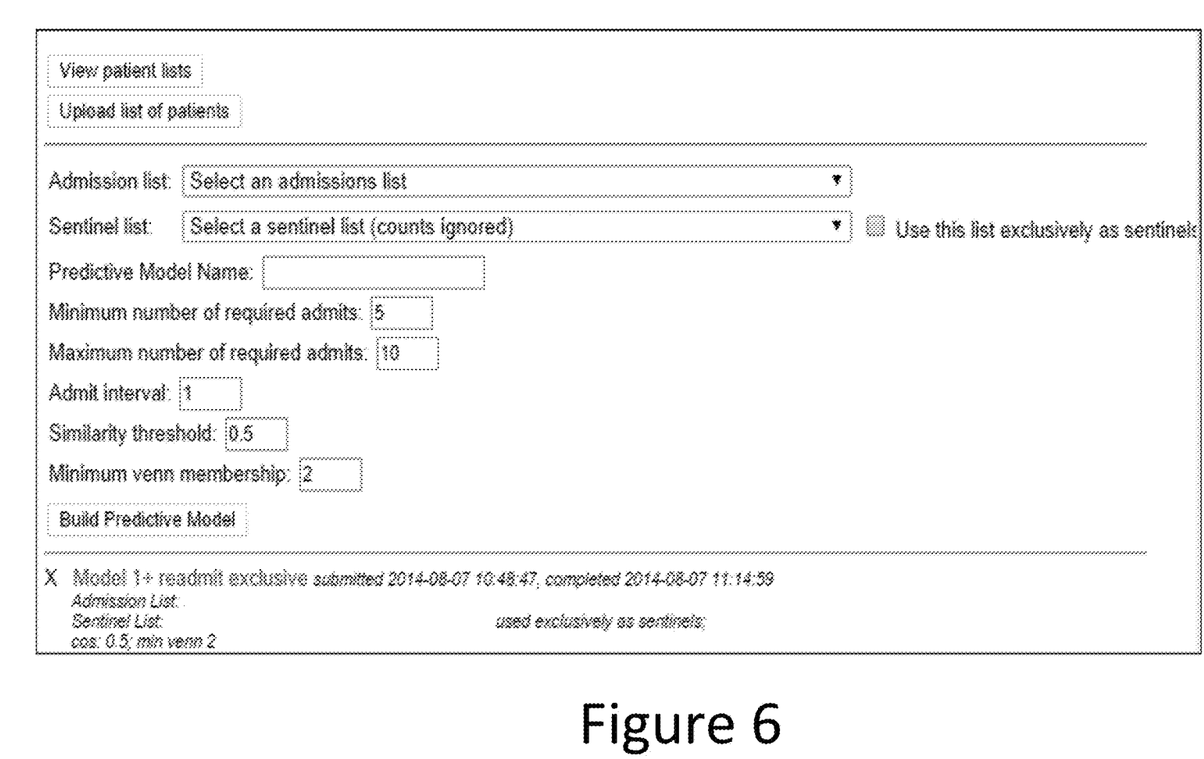
FIG. 6 is an embodiment of the present invention that allows users to select a training population, specify model parameters, and execute the predictive model on a new target population.

FIG. 6 shows an example screenshot of the system, in which the users are able to provide a list of patients and outcome values, select a training population, and assign threshold values for parameters of the model.

Figure 7:
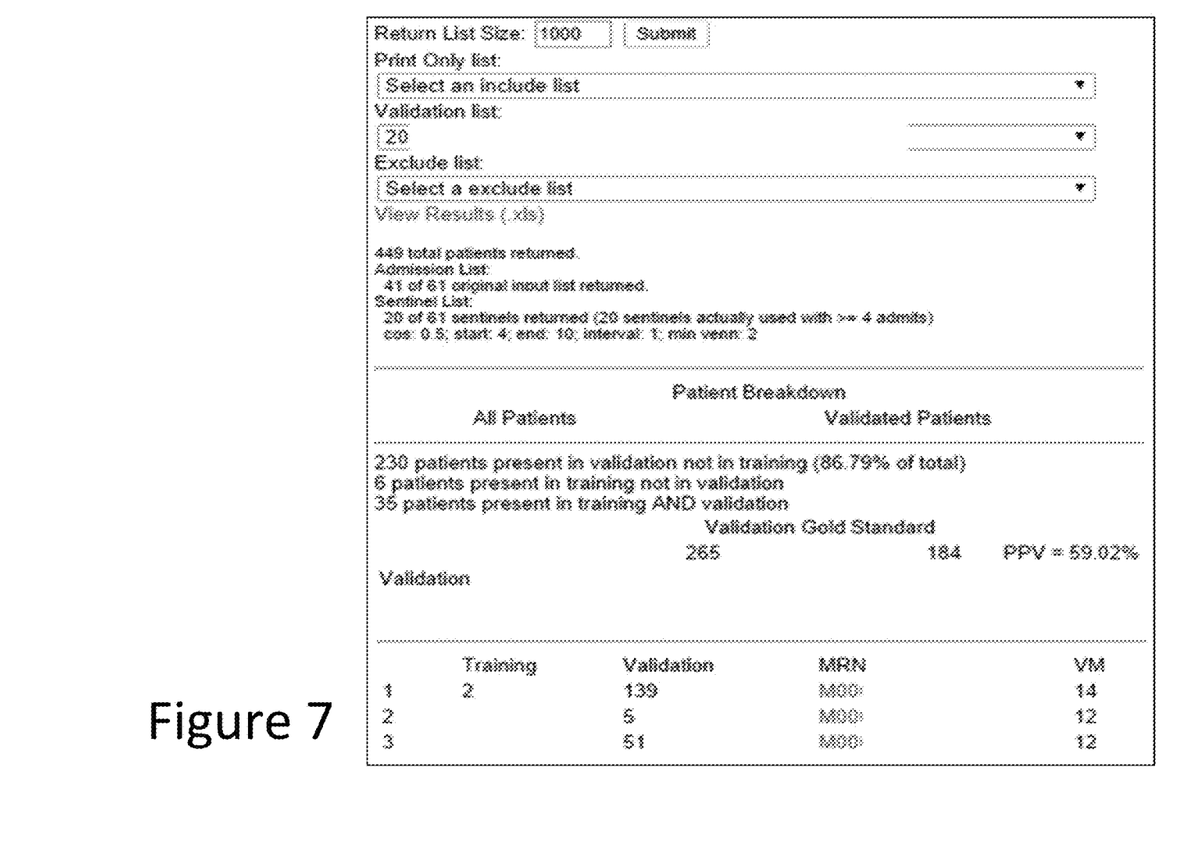
FIG. 7 is an embodiment of the present invention that displays the output of optimized model on selected population.

FIG. 7 shows an example screenshot of the system, in which users may select a population for validation of the model so that the method of the present invention can produce performance metrics (such as positive predictive value, counts, memberships, etc.) on this dataset. The performance (positive predictive value and odds ratio) of the predictive modeling system is shown in Table 1. In general, the model predicts outcomes at a level much higher than random chance. As an example, the performance of the model is shown for three different patient populations in Table 1, below:

TABLE 1

Performance of Predictive Modeling System for Three Patient Populations

| Condition | Population | Baseline Incidence | Positive Predictive Value | Odds Ratio |
| --- | --- | --- | --- | --- |
| Hospital Admission | Medicare | 14.8% | 40.5% | 2.74 |
| Hospital Admission | Oncology | 34.8% | 49.2% | 1.41 |
| Hospital Admission | Emergency Dept. | 40.7% | 69% | 1.70 |

INDUSTRIAL APPLICABILITY

The present invention is a method implemented on a computer that concatenates patient medical records, summarizes patient medical records, and provides condition-specific predictions about the patients based on their medical history.

Although the present invention has been described and illustrated with respect to a preferred embodiment and a preferred use therefor, it is not to be so limited since modifications and changes can be made therein which are within the full intended scope of the invention.

We claim:

1. An optimizing process for optimizing a predictive modeling method implemented on a computer for predicting patient outcomes and conditions from medical database records of a population of patients, said predictive modeling method comprising the steps of:
   (a) providing medical database records of a population of patients, each patient of
      said population of patients having corresponding outcome health score values;
   (b) processing said medical database records by using Natural Language Processing;
   (c) building a patient document corpus from said medical database records processed
      by using Natural Language Processing;
   (d) weighting terms in said corpus by assigning a weight to each term in the corpus,
      said weight representing said term's frequency for a patient's document with
      respect to said term's frequency across all documents in said corpus;
   (e) Constructing a high-dimensional and sparse term-by-document matrix from said
      weighted terms, each said term in said corpus being represented as a vector across
      said population of patients;
   (f) performing matrix factorization of said term-by-document matrix using Latent
      Semantic Indexing to reduce the dimensionality of said term-by-document matrix
      into a lower-dimensional matrix concept space;
   (g) querying said lower-dimensional matrix concept space using a term or
      combination of terms to produce a single ranking of patients in said corpus using
      a similarity score;
   (h) given a single threshold of said similarity score, combining multiple said single
      rankings to re-rank said population of patients in said corpus based on relatedness
      to multiple queries;
   (i) optimizing said predictive modeling method through iterative variation of certain
      parameters to achieve a best precision fit, said certain parameters comprising:
      (1) the number of patients used for each said query of said multiple queries;
      (2) said threshold of said similarity score;
      (3) a frequency of association to query of said patients of said corpus;
      (4) a recall value of said patients returned by said query; and
      (5) a precision value of said patients returned by said query; and
      transmitting data associated with optimized re-ranked population of patients to one or more practitioners.

2. The optimizing process of claim 1, where said processing of said medical database records is performed by concatenation of unstructured text fields from said individual patient's medical records, and where processing said medical database records by using Natural Language Processing is performed on individual patient documents.

3. The optimizing process of claim 1, where said lower-dimensional matrix concept space is queried using a given patient's document in said corpus to rank other patient's documents in said corpus to produce a ranking of said other patients in said corpus using said similarity score.

* * * * *